US005649976A

United States Patent [19]

Malewicz

[11] Patent Number: 5,649,976

[45] Date of Patent: *Jul. 22, 1997

[54] NEUROMUSCULAR STIMULATOR ELECTRODE

[75] Inventor: Andrzej Malewicz, Minneapolis, Minn.

[73] Assignee: Empi, Inc., St. Paul, Minn.

[*] Notice: The term of this patent shall not extend beyond the expiration date of Pat. No. 5,464,448.

[21] Appl. No.: 529,151

[22] Filed: Sep. 15, 1995

Related U.S. Application Data

[63] Continuation of Ser. No. 236,341, May 2, 1994, Pat. No. 5,464,448.

[51] Int. Cl.⁶ .................................................. A61N 1/05
[52] U.S. Cl. .................................... 607/138; 607/41
[58] Field of Search ................................ 607/35–41, 138

[56] References Cited

U.S. PATENT DOCUMENTS

| | | | |
|---|---|---|---|
| 1,704,000 | 3/1929 | Herwig et al. | 607/138 |
| 2,085,644 | 6/1937 | Ferciot | 607/138 |
| 2,126,257 | 9/1938 | Hird . | |
| 3,650,275 | 3/1972 | Von Der Mozel | 607/138 |
| 3,800,800 | 4/1974 | Garbe et al. | 128/408 |
| 4,106,511 | 8/1978 | Erlandsson | 128/407 |
| 4,881,526 | 11/1989 | Johnson et al. | 128/24.5 |
| 5,199,443 | 4/1993 | Maurer et al. | 128/138 |
| 5,199,543 | 4/1993 | Kamagami et al. | 194/207 |
| 5,314,465 | 5/1994 | Maurer et al. | 607/138 |
| 5,370,671 | 12/1994 | Maurer et al. | 607/138 |
| 5,376,206 | 12/1994 | Maurer et al. | 24/883 |
| 5,385,577 | 1/1995 | Maurer et al. | 607/138 |

FOREIGN PATENT DOCUMENTS

| | | |
|---|---|---|
| 0178514 | 4/1986 | European Pat. Off. . |
| 0 219 410 A1 | 4/1987 | European Pat. Off. . |
| 4022074 A1 | 2/1992 | Germany . |

OTHER PUBLICATIONS

*The Shape of Anal Electrode*, Alexander Perelman, M.D., Ph.d., Sep. 14, 1993.
*Electrical Treatment of Incontinence*, Brit. J. Surg. 1967, vol. 54, No. 9, Sep.
*The Pressure Exerted by the External Sphincter of the Urethra When Its Motor Nerve Fibers Are Stomulated Eelectricity*, British Journal of Urology, (1974), 46, 453–462.
*Effects of External and Direct Pudendal Nerve Maximal Electrical Stimulation in the Treatment of the Uninhibits Overactive Bladder*, British Journal of Urology (1989), 64, 374–380.
*Management of Urinary Incontinence with Electronic Stimulation: Observations and Results*, The Journal of Urology vol. 116, Dec.
*The Treatment of Femal Urinary Incontinence by Functional Electrical Stimulation*, Urogynecology and Urodynamics Ed. by D.R. Ostergard and A.E. Bent, 1991.
*Treatment of Urinary Incontinence by External Stimulating Devices*, Urol. Int. (1974), 29, 450–457.

Primary Examiner—Lee S. Cohen
Attorney, Agent, or Firm—Kinney & Lange, P.A.

[57] ABSTRACT

A method for manufacturing an electrode comprises molding a plurality of spaced conductive sections which include a pin receptacle for receiving a connector pin of a wire harness. A skeleton of conductive sections, connector pins and lead wires are placed in a mold which defines the electrode. A non-conductive polymer is molded to the skeleton to form an integral electrode having a elongated body of conductive sections separated by non-conductive sections. Multiple durometer polymers may be used to achieve desired levels of flexibility of the electrode.

10 Claims, 3 Drawing Sheets

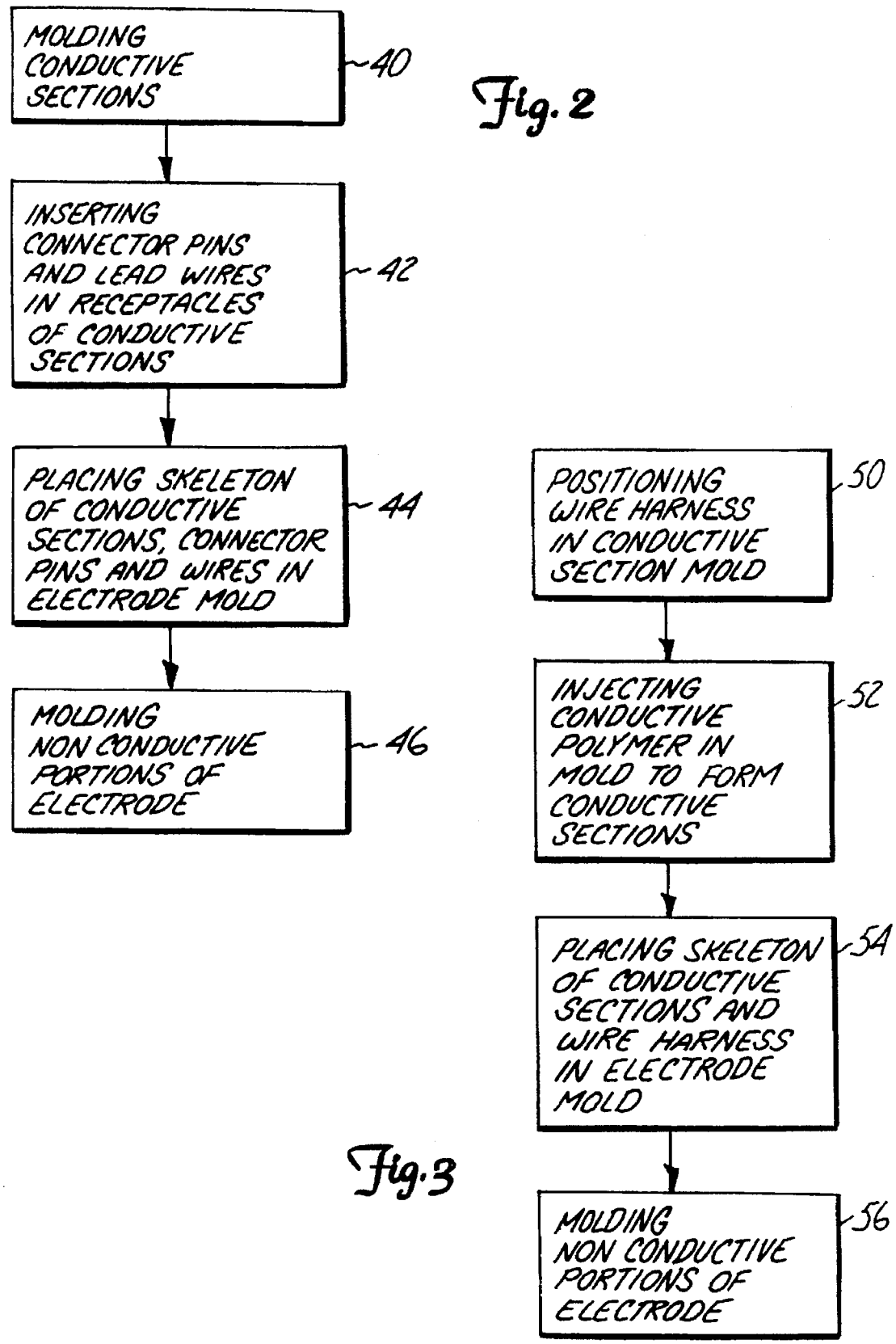

NEUROMUSCULAR STIMULATOR ELECTRODE

This is a continuation of application Ser. No. 08/236,341, filed May 2, 1994, now U.S. Pat. No. 5,464,448.

BACKGROUND OF THE INVENTION

The present invention relates generally to the field of electrical neuromuscular stimulation for the treatment of incontinence. In particular, the present invention is a method of construction for a solid, molded electrode having increased effectiveness.

Electrical neuromuscular stimulation is widely used to assist persons afflicted with motor dysfunctions in performing muscle contraction maneuvers. Motor nerve fibers are electrically stimulated by means of transcutaneously applied pulses of electrical current to cause contractions of the innervated muscles. This technique is also used to re-educate patients in the proper use of dysfunctional muscles.

For example, in cases in which urinary incontinence in women is caused by the patient's inability to properly contract the external sphincter of the urethra, it has been shown that neuromuscular stimulation of the dysfunctional muscles by means of a vaginal electrode can effectively prevent the unwanted flow of urine. By use of such an electrode, some patients can educate themselves to voluntarily or automatically impede the flow of urine.

A more important application of pelvic force stimulation is the exercise and toning of the muscles of the pelvic floor which support the bladder, the vagina, urethra and other organs. Muscles which have become lax or stretched through the process of child birth or natural aging, can be strengthened and tightened to properly support these structures, thus positively affecting the patient's ability to maintain continence.

Electrical stimulators for controlling incontinence generally include a plug with one or more electrodes in the form of conductive metal rings or polymer bands. A wire harness, including connector pins and lead wires, extends from the plug to a controller or stimulator which generates stimulation signals. The controller is usually worn externally, attached to the user's clothing.

There is a continuing need for a lightweight, flexible device which can re-train the dysfunctional muscles responsible for incontinence. In addition to being effective, the stimulator must be durable, hygienic and inexpensive to manufacture.

SUMMARY OF THE INVENTION

The present invention is an improved method of manufacturing a solid, yet flexible, electrode adapted for insertion into a body cavity for stimulating and constricting the muscles adjacent the cavity, in order to retrain the muscles and prevent incontinence. An electrode made in accordance with the method of the present invention includes an elongated contoured body, handle and bulbous end molded from a relatively compliant non-conductive polymer. The elongated body includes a plurality of conductive sections which are formed from a conductive polymer. The conductive sections are spaced along a longitudinal axis of the elongated body. Electrical connectors may be molded with or inserted into each conductive section to form a secure and durable mechanical/electrical connection.

The method of the present invention includes forming a skeleton of conductive sections, connector pins and lead wires. The conductive sections are made by molding a conductive polymer to define an annular shape and include a pin receptacle. An electrical connector pin and its corresponding lead wire is positioned within the receptacle. The resulting skeleton of conductive sections, connector pins and lead wires is placed in a mold which defines the general shape of the electrode. A non-conductive polymer is then molded to the skeleton to form an integral electrode.

In a first embodiment of the method of the present invention, forming the skeleton includes molding each conductive section and then inserting an electrical connector pin and corresponding lead wire into an appropriate receptacle in each conductive section.

In a second embodiment of the method of the present invention, forming the skeleton includes molding the connector pins and lead wires into the conductive sections. More particularly, the wire harness (i.e. the connector pins and corresponding lead wires) is positioned within the mold for the conductive sections. As each conductive section is molded, the conductive polymer surrounds the electrical components so that the result is the skeleton of conductive sections, connector pins and lead wires.

BRIEF DESCRIPTION OF THE DRAWINGS;

FIG. 2 shows the steps of the first embodiment of the method of the present invention.

FIG. 3 shows the steps of the second embodiment of the method of the present invention.

DETAILED DESCRIPTION OF THE PREFERRED EMBODIMENTS

Figure 1:
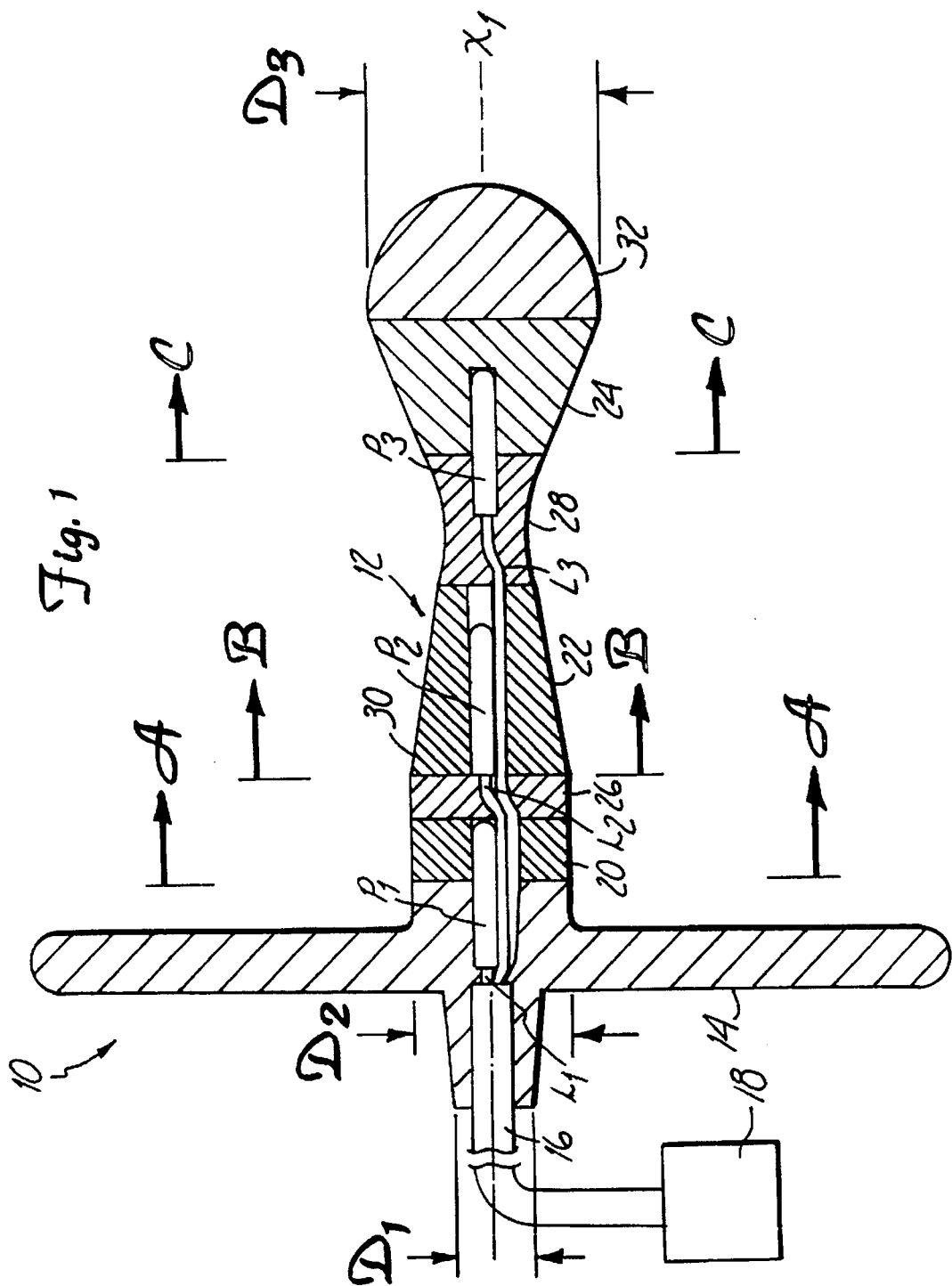
FIG. 1 shows a side view of an electrode made in accordance with the method of the present invention.

FIG. 1 is a side view of a preferred embodiment of an electrode made in accordance with the methods of the present invention. Electrode 10 is used for muscle stimulation within a body cavity and generally includes elongated contoured body 12, handle 14, electrical wire harness 16 and electrical stimulation controller 18. Elongated body 12 includes first conductive section 20, second conductive section 22, third conductive section 24, non-conductive sections 26 and 28 and bulbous end 32, all of which are longitudinally spaced along axis $X_1$.

Wire harness 16 extends from sleeve 15 of handle 14 and delivers leads $L_1$, $L_2$ and $L_3$ to elongated body 12 of electrode 10. Each lead wire is attached to a pin connector by any acceptable manner, such as crimping and/or soldering. Pin connectors $P_1$, $P_2$, and $P_3$ are formed of metal, such as gold coated brass.

Also shown are an inner diameter $D_1$ of 0.250 inches, an outer diameter $D_2$ of 0.500 inches and an end diameter $D_3$ of approximately 0.750 inches. The overall length of electrode 10, measured along axis $X_1$ from sleeve 15 to bulbous end 32, is approximately 2.5 to 3.0 inches.

Elongated body 12 has an hourglass-like shape with outer surface 30 being radially tapered through regions 22, 24 and 28. Body 12 has a narrow waist region (i.e. non-conductive section 28) having a minimum diameter of 0.265 inches.

Elongated body 12 is contoured to provide bulbous end 32, which facilitates a traumatic insertion of electrode 10 within a body cavity. When electrode 10 is positioned within a body cavity adjacent the dysfunctional muscles, electrical current from controller 18 is delivered to conductive sections 20, 22 and 24 via wire harness 16. This electrical current induces the muscles to contract causing the surrounding muscles to bear down on body 12 in a non-uniform manner so as to conform to the hourglass shape of exterior surface 30. The hourglass (i.e. contoured) shape of body 12 thereby aids in maintaining electrode 10 in a desired location.

Figure 1A:
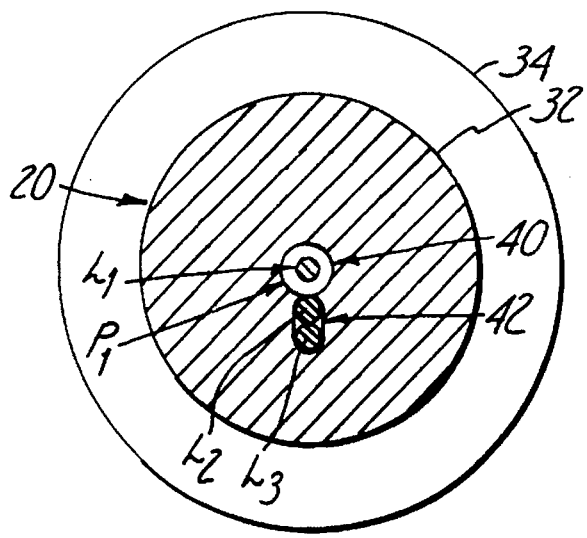
FIG. 1A is a cross-sectional view of the electrode taken along line A—A of FIG. 1.

FIG. 1A shows a cross-sectional view of electrode 10 taken along line A—A of FIG. 1. Connector pin $P_1$, its accompanying lead wire $L_1$ and lead wires $L_2$ and $L_3$ are shown positioned within pin receptacle 40 and wire receptacle 42, respectively in conductive section 20. More particularly, lead $L_1$ extends from connector pin $P_1$. Lead wires $L_2$ and $L_3$, are connected to pins $P_2$ and $P_3$ (not shown), respectively.

In this embodiment, lead wires $L_1$ and $L_2$ are positioned below connector pin $P_1$. The location of the lead wires and connector pins, however, is dependent upon the position of the receptacles in the conductive sections. Each receptacle has a longitudinal axis parallel to longitudinal axis $X_1$ of elongated body 12. Pin receptacle 40 is directly above wire receptacle 42. However, the pin and wire receptacles may be in any configuration which allows each pin receptacle to be in communication with each wire receptacle in the same conductive section. Solid line 32 represents outer diameter $D_2$ of electrode 10 while solid line 34 is end diameter $D_3$ which is defined by bulbous end 32.

Figure 1B:
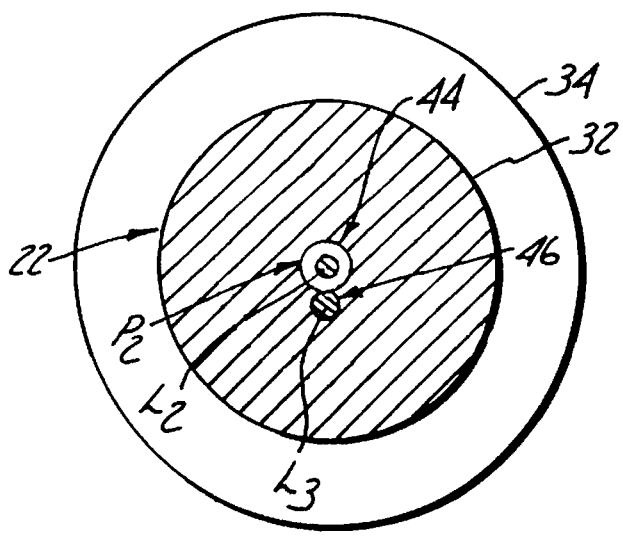
FIG. 1B is a cross-sectional view of the electrode taken along line B—B of FIG. 1.

FIG. 1B shows a cross-sectional view of electrode 10 taken along line B—B of FIG. 1. In this view, connector pin $P_2$ and lead wires $L_2$ and $L_3$ are shown within second conductive section 22. Lead wire $L_2$ extends from connector pin $P_2$ while lead wire $L_3$ is shown positioned below pin $P_2$. As shown in the figure, pin $P_2$ is press fit within pin receptacle 44 and wire $L_3$ is positioned within wire receptacle 46. Receptacles 44 and 46 must be in communication with each other. As in the previous figure, solid line 32 is outer diameter $D_2$ and solid line 34 is end diameter $D_3$ of electrode 10.

Figure 1C:
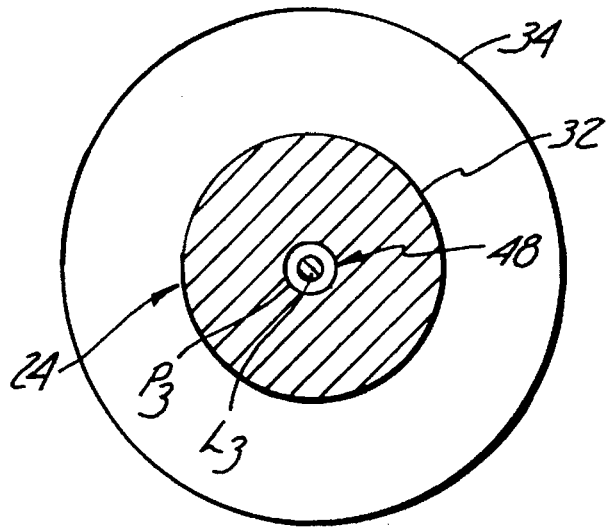
FIG. 1C is a cross-sectional view of the electrode taken along line C—C of FIG. 1.

FIG. 1C shows a cross-sectional view of electrode 10 taken along line C—C of FIG. 1. Connector pin $P_3$ and lead wire $L_3$ are shown press fit within pin receptacle 48 in third conductive section 24. Lead wire $L_3$ extends from connector pin $P_3$. Also shown is solid line 32 representing outer diameter $D_2$ and solid line 34 which is end diameter $D_3$. $L_3$ extends from connector pin $P_3$. Also shown is solid line 32 representing outer diameter $D_2$ and solid line 34 which is end diameter $D_3$.

FIG. 2 shows the steps of a first embodiment of the method for manufacturing electrode 10 in accordance with the present invention.

In step 40, first conductive section 20, second conductive section 22 and third conductive 24 are molded. In this embodiment of the method, the conductive sections are formed by injecting a medical grade thermoset conductive polymer, such as Rhodorsil RS 1316, into molds which define the shape of each conductive section. The conductive sections are injection molded (or molded by any acceptable processing technique) at a temperature of 350° F. and then post cured for approximately 16 hours, so that the annular shape of the conductive section may be retained. The resulting conductive sections 20, 22 and 24 have a durometer of 65 shore A and a volume resistivity of approximately 5.5 ohm-cm. Although, the diameter of second conductive section 22 and third conductive section 24 may vary because these sections are tapered to produce the hourglass-like shape of elongated body 12, the greatest diameter of any molded conductive section is approximately 0.500–0.600 inches.

Each conductive section includes a pin receptacle. First conductive section 20 and second conductive section 22 also include wire receptacles. The dimensions of the pin receptacle and the wire receptacle, however, may change in accordance with the brand of the electrical component used. In this embodiment, the mold for first conductive section 20 defines a pin receptacle 40 having a diameter of 0.076 inches. A smaller elliptical wire receptacle 42 has a major axis of 0.04 inches and minor axis of 0.020 inches. Receptacles 40 and 42 receive connector pin $P_1$/lead wire $L_1$ and lead wires $L_2$ and $L_3$, respectively. Receptacle 40 opens into receptacle 42 so that the two receptacles are in communication with each other within first conductive section 20 (see FIG. 1A).

The mold for second conductive section 24 includes pin receptacle 44 and wire receptacle 46. However, wire receptacle 46 receives only one wire ($L_3$) in conductive section 22. Thus, wire receptacle 46 has a diameter of 0.020 inches in second conductive section 24. Pin receptacle 44 has the same diameter as pin receptacle 40. As in first conductive section 20, receptacles 44 and 46 are arranged so that they are in communication with each other (see FIG. 1B).

The mold for third conductive section 24 includes a single blind or through pin receptacle 48 having a diameter of 0.076 inches. Pin receptacle 48 receives connector pin $P_3$ and its accompanying lead wire $L_3$. (see FIG. 1C).

In step 42, connector pins $P_1$, $P_2$, and $P_3$ and their attached lead wires $L_1$, $L_2$ and $L_3$, respectively are inserted into the appropriate receptacles in each conductive section.

Each connector pin has a diameter slightly larger than the diameter of each pin receptacle. Although each connector pin may still pass through a pin receptacle when sufficient force is applied in a longitudinal direction, the larger diameter of the connector pins provides a durable mechanical/ electrical connection between the conductive section and the connector pin. Thus, despite "stress creep" (elastomeric relaxation) of the polymer compounds of electrode 10, or flexing of electrode 10 due to the contractive forces of the surrounding muscles, the insertion of pin connectors $P_1$–$P_3$ into their respective receptacles provides a continuous mechanical and electrical contact.

In accordance with step 42, pin $P_3$ and its attached lead wire $L_3$ are fed through pin receptacle 40 in first conductive section 20 and pin receptacle 44 in second conductive section 22 so that pin $P_3$ may be permanently inserted into pin receptacle 48 in third conductive section 24.

Upon insertion of pin $P_3$ into pin receptacle 48, however, lead wire $L_3$ is still positioned within pin receptacles 40 and 44. Therefore, lead wire $L_3$ must be manually pushed into wire receptacle 42 in first conductive section 20 and wire receptacle 46 in second conductive section 22 so that it is press fit into the appropriate wire receptacle in first conductive section 20 and second conductive section 22.

Next, connector pin $P_2$ and its attached lead wire $L_2$ are fed through pin receptacle 40 in first conductive section 20 so that connector pin $P_2$ may be permanently inserted into pin receptacle 44 in second conductive section 22. Upon insertion of pin $P_2$ into pin receptacle 44, however, lead wire $L_2$ is still positioned within pin receptacle 40 in first conductive section 20. Therefore, lead wire $L_2$ must be manually pushed into wire receptacle 42 in first conductive section 20. In a final insertion step, connector pin $P_1$ and its attached lead wire $L_1$ are inserted into pin receptacle 40 in first conductive section 20.

In step 44, the skeleton including first conductive section 20, second conductive section 22, third conductive section 24 and their respective connector pins/lead wires is positioned within a second mold defining elongated body 12, handle 14 and bulbous end 32 of electrode 10.

In step 46, a medical grade non-conductive polymer, such as Dow-Corning Silastic Q-7-4565 combined with a catalyst such as dicumyl peroxide, is injected (or molded by any acceptable processing technique) into the second mold in regions which define handle 14 non-conductive sections 26 and 28 and bulbous end 32. Non-conductive sections 26 and 28 are molded to connect with conductive sections 20, 22 and 24 so that elongated body 12 of electrode 10 is formed. After molding each non-conductive portion, electrode 10 is cured for approximately 2 hours at 350° F. to effect the chemical bonding of conductive sections 20, 22 and 24 to non-conductive sections 26 and 28 and to retain the general shape of elongated body 12, handle 14 and bulbous end 32. The non-conductive portions of the electrode have a durometer of about 67 shore A.

FIG. 3 shows the steps of a second method for manufacturing electrode 10 in accordance with the present invention.

In step 50, wire harness 16 is placed within a first mold which defines first conductive section 20, second conductive section 22 and third conductive section 24.

In step 52, a conductive polymer such as Santoprene 199-87 (a thermoplastic polymer) is used to mold the first, second and third conductive sections. More particularly, Santoprene is injection molded (or molded by any other acceptable processing technique) at approximately 375° F. Each resulting conductive section has a durometer of 87 shore A and a volume resistivity of 100–200 ohm-cm.

The conductive polymer actually molds around the wire harness such that it surrounds connector pins $P_1$, $P_2$, $P_3$ and lead wires $L_1$, $L_2$ and $L_3$ so that receptacles are not required in the conductive sections. Hence, there is no need to insert electrical components into each conductive section.

In step 54, the resulting skeleton including first conductive section 20, second conductive section 22, third conductive section 24 and wire harness 16 is positioned in a second mold which defines elongated body 12, handle 14 and bulbous end 32 of electrode 10.

In step 56, a non-conductive polymer such as thermoplastic Santoprene 281-87 is molded at a temperature between 350°–450° F. into regions of the second mold which define non-conductive portions of electrode 10. Non-conductive sections 26 and 28 are molded to connect first conductive section 20, second conductive section 22 and third conductive section 24 to form elongated body 12 of electrode 10. Santoprene 281-87 is also used to mold the regions which define handle 14 and bulbous end 32. Each non-conductive section has a durometer of 87 shore A.

An electrode made in accordance with the method of the present invention may be of a single or dual durometer. A single durometer electrode implies that the electrode is made of polymers which have the same durometer and hence, the same amount of flexibility throughout the electrode. A dual durometer electrode, however, implies that polymers of differing durometer are used to fabricate the electrode.

For example, in an alternative embodiment, a non-conductive polymer having a durometer ranging from 75–87 Shore A may be used to mold the narrow waist area of the electrode (i.e. non-conductive section 28) while a non-conductive polymer having a durometer ranging from 65–70 Shore A may be injected at the bulbous end and handle area of the same electrode. In this manner, precise bending stiffness is provided at the waist area while perceived comfort for the patient is enhanced at the bulbous end and handle area. Other variations of multiple durometer electrodes may be employed to obtain a desired level of flexibility of the electrode.

The method of the present invention teaches a process for manufacturing a solid electrode which does not require labor intensive mechanical/electrical connections. The resulting electrode is a solid, yet flexible, device which provides reliable neuromuscular stimulation and a hygienic appearance with prolonged use.

Although the present invention has been described with reference to preferred embodiments, workers skilled in the art will recognize that changes may be made in form and detail without departing from the spirit and scope of the invention.

What is claimed is:

1. A neuromuscular stimulator electrode comprising:

an elongated contoured solid body including a plurality of spaced conductive sections molded from a conductive polymer;

a plurality of spaced non-conductive sections molded from a non-conductive polymer, wherein the non-conductive sections are interposed between the conductive sections; and a wire harness comprising a plurality of wire leads, wherein at least one of the plurality of wire leads is positioned within each of the conductive sections.

2. The neuromuscular stimulator electrode of claim 1 wherein the contoured body has an hour-glass shape.

3. The neuromuscular stimulator electrode of claim 1 wherein the plurality of spaced conductive sections comprises three conductive sections.

4. The neuromuscular stimulator electrode of claim 1 wherein the conductive polymer has a volume resistivity in the range of 5–200 ohm-centimeters.

5. The neuromuscular stimulator electrode of claim 1 wherein each of the non-conductive sections is defined by a side wall and a passage for positioning at least one of the plurality of wire leads, and further wherein at least one of the non-conductive sections has a sidewall thickness which is greater than a diameter of the passage.

6. A neuromuscular stimulator electrode comprising:

an elongated solid body having a length in the range of 2.5 inches to 3 inches, and further having a contoured hour-glass shape, the elongated body including three injection molded spaced conductive polymer sections, the spaced conductive polymer sections separated by non-conductive polymer;

a wire harness comprising three wire leads, wherein each wire lead is positioned within a corresponding conductive polymer section, the wire leads extending from an end of the electrode for connection to a controller.

7. The neuromuscular stimulator electrode of claim 6, wherein the conductive polymer sections have a volume resistivity in the range of 5 ohm-centimeters to 200 ohm-centimeters.

8. The neuromuscular stimulator electrode of claim 6, wherein the hour-glass shaped body of the electrode includes a waist having a diameter of at least 0.265 inches.

9. The neuromuscular stimulator electrode of claim 6, wherein the conductive polymer sections have a diameter of at least 0.500 inches.

10. The neuromuscular stimulator electrode of claim 6 wherein the non-conductive polymer defines a side wall and a passage for positioning at least one of the three wire leads, and further wherein a thickness of the side wall is greater than a diameter of the passage.

* * * * *

UNITED STATES PATENT AND TRADEMARK OFFICE
CERTIFICATE OF CORRECTION

PATENT NO. : 5,649,976
DATED : July 22, 1997
INVENTOR(S) : Andrzei Malewicz

It is certified that error appears in the above-identified patent and that said Letters Patent is hereby corrected as shown below:

Column 6, line 11, delete "an", insert --art--.

Signed and Sealed this

Tenth Day of February, 1998

Attest:

BRUCE LEHMAN

Attesting Officer

Commissioner of Patents and Trademarks